United States Patent
Ho

(10) Patent No.: US 9,216,264 B2
(45) Date of Patent: Dec. 22, 2015

(54) PORTABLE PATIENT INTERFACE SYSTEM

(75) Inventor: Peter Chi Fai Ho, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 273 days.

(21) Appl. No.: 13/813,980

(22) PCT Filed: Jul. 13, 2011

(86) PCT No.: PCT/IB2011/053122
§ 371 (c)(1),
(2), (4) Date: Feb. 4, 2013

(87) PCT Pub. No.: WO2012/020339
PCT Pub. Date: Feb. 16, 2012

(65) Prior Publication Data
US 2013/0152936 A1 Jun. 20, 2013

Related U.S. Application Data

(60) Provisional application No. 61/371,874, filed on Aug. 9, 2010.

(51) Int. Cl.
*A61M 16/06* (2006.01)
*A61M 16/08* (2006.01)
*A61M 16/00* (2006.01)

(52) U.S. Cl.
CPC ........... *A61M 16/06* (2013.01); *A61M 16/0057* (2013.01); *A61M 16/0633* (2014.02); *A61M 16/0875* (2013.01)

(58) Field of Classification Search
CPC ........... A61D 7/00; A61D 7/04; A61M 15/00; A61M 16/00; A61M 16/0045; A61M 16/0048; A61M 16/0057; A61M 16/0078; A61M 16/0081; A61M 16/0084; A61M 16/01; A61M 16/06; A61M 16/0611; A61M 16/0616; A61M 16/0633; A61M 16/0638; A61M 16/0666; A61M 16/0683; A61M 16/08; A61M 16/0825; A61M 16/0875; A61M 16/10; A61M 16/105; A61M 16/20; A61M 16/204; A61M 16/205; A61M 16/208; A62B 18/00; A62B 18/02; A62B 18/025; A62B 18/08; A62B 7/00; A62B 7/02; B64D 10/00; B64G 1/22; B64G 1/60; C23C 16/4412; F16L 3/13
USPC ............ 128/200.24, 201.22, 201.23, 202.13, 128/202.28, 202.29, 203.11, 203.12, 128/203.28, 203.29, 204.18, 205.13, 128/205.16, 205.17, 205.25, 206.21, 128/206.22, 206.24, 206.26, 206.27, 128/206.28, 207.11, 207.13, 911, 914
See application file for complete search history.

(56) References Cited

U.S. PATENT DOCUMENTS

| | | | | |
|---|---|---|---|---|
| 4,437,462 A | * | 3/1984 | Piljay et al. | 128/207.11 |
| 4,685,456 A | * | 8/1987 | Smart | 128/205.22 |

(Continued)

FOREIGN PATENT DOCUMENTS

| | | | |
|---|---|---|---|
| GB | 2365777 A | * | 2/2002 |
| WO | WO01/87396 A1 | * | 11/2001 |
| WO | WO2010067236 A1 | | 6/2010 |

*Primary Examiner* — Annette Dixon
(74) *Attorney, Agent, or Firm* — Michael W. Haas

(57) ABSTRACT

A portable patient interface system (2) includes a frame (16), a cushion (14) coupled to a first side of the frame, a collapsible faceplate (18) coupled to a second side of the frame opposite the first side, and a longitudinally collapsible hose (56) structured to be in fluid communication with the collapsible faceplate and the cushion.

10 Claims, 4 Drawing Sheets

(56) References Cited

U.S. PATENT DOCUMENTS

| | | |
|---|---|---|
| 5,121,745 A | 6/1992 | Israel |
| 5,662,101 A * | 9/1997 | Ogden et al. ............. 128/205.25 |
| 5,921,239 A * | 7/1999 | McCall et al. ........... 128/205.25 |
| 6,079,410 A * | 6/2000 | Winefordner et al. ... 128/201.11 |
| 6,119,693 A * | 9/2000 | Kwok et al. ............. 128/207.11 |
| 2007/0107733 A1 | 5/2007 | Ho |
| 2009/0078259 A1 | 3/2009 | Kooij |

* cited by examiner

PORTABLE PATIENT INTERFACE SYSTEM

CROSS-REFERENCE TO RELATED APPLICATIONS

This patent application claims the priority benefit under 35 U.S.C. §371 of international patent application no. PCT/IB2011/053122, filed Jul. 31, 2011, which claims the priority benefit under 35 U.S.C. §119(e) of U.S. Provisional Application No. 61/371,874 filed on Aug. 9, 2010, the contents of which are herein incorporated by reference.

BACKGROUND OF THE INVENTION

1. Field of the Invention

The present invention relates to non-invasive ventilation and pressure support systems, and in particular to a portable patient interface system that may be used with non-invasive ventilation and pressure support systems.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping.

Non-invasive ventilation and pressure support therapies as just described involve the placement of a patient interface device including a mask component having a soft, flexible cushion on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. Such patient interface devices may also employ other patient contacting components, such as forehead supports, cheek pads and chin pads. The patient interface device is connected to a gas delivery hose and interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Patients suffering from OSA or similar disorders require ongoing treatment (e.g., CPAP treatment) to maintain a healthful routine. Thus, for patients that travel frequently and are away from home for long periods, the portability of the mask and gas delivery hose is vital for therapy compliance. This is especially true for those patients that frequently travel by air, as tightened airport security and restrictions in luggage allowance (both carry-on and checked) are making it more difficult to travel with pressure support therapy equipment. While the size of the pressure generating machine portion of such equipment (e.g., the CPAP machine) has reduced significantly in recent years, the size mask and the hose portions have not. In addition, it is often not just the size of the mask and hose that matter; the lack of effective packaging for the equipment is also a factor. Furthermore, a 6-foot long gas delivery hose is standard for many treatment systems and such a hose is particularly cumbersome when it comes to packing.

SUMMARY OF THE INVENTION

Accordingly, it is an object of the present invention to provide a portable patient interface system that overcomes the shortcomings of conventional patient interface systems. This object is achieved according to one embodiment of the present invention by providing a portable patient interface system that includes a frame, a cushion coupled to a first side of the frame, a collapsible faceplate coupled to a second side of the frame opposite the first side, and a longitudinally collapsible hose structured to be in fluid communication with the collapsible faceplate and the cushion.

In another embodiment, a hose assembly for a patient interface device is provided that includes a longitudinally collapsible hose, a first tube portion coupled to the longitudinally collapsible hose, and a second tube portion coupled to the longitudinally collapsible hose, wherein the first tube portion and the second tube portion are selectively connectable to one another, and wherein the longitudinally collapsible hose, when collapsed, is structured to be held within the first tube portion and the second tube portion. The hose assembly may be offered and provided to a patient separately from any particular patient interface device.

In still another embodiment, a patient interface device is provided that includes a frame, a cushion coupled to a first side of an annular portion of the frame, and a collapsible faceplate having a first side coupled to a second side of the annular portion of the frame opposite the first side of the annular portion of the frame, wherein a second side of the collapsible faceplate is structured to be fluidly coupled to a fluid coupling connector, and wherein the collapsible faceplate is structured to be collapsed and received within a chamber defined by an interior of the cushion and the annular portion responsive to a force being applied to the collapsible faceplate. The patient interface device of this embodiment may be offered and provided to a patient separately from any particular gas delivery hose or hose assembly.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF THE EXEMPLARY EMBODIMENTS

Figure 1:
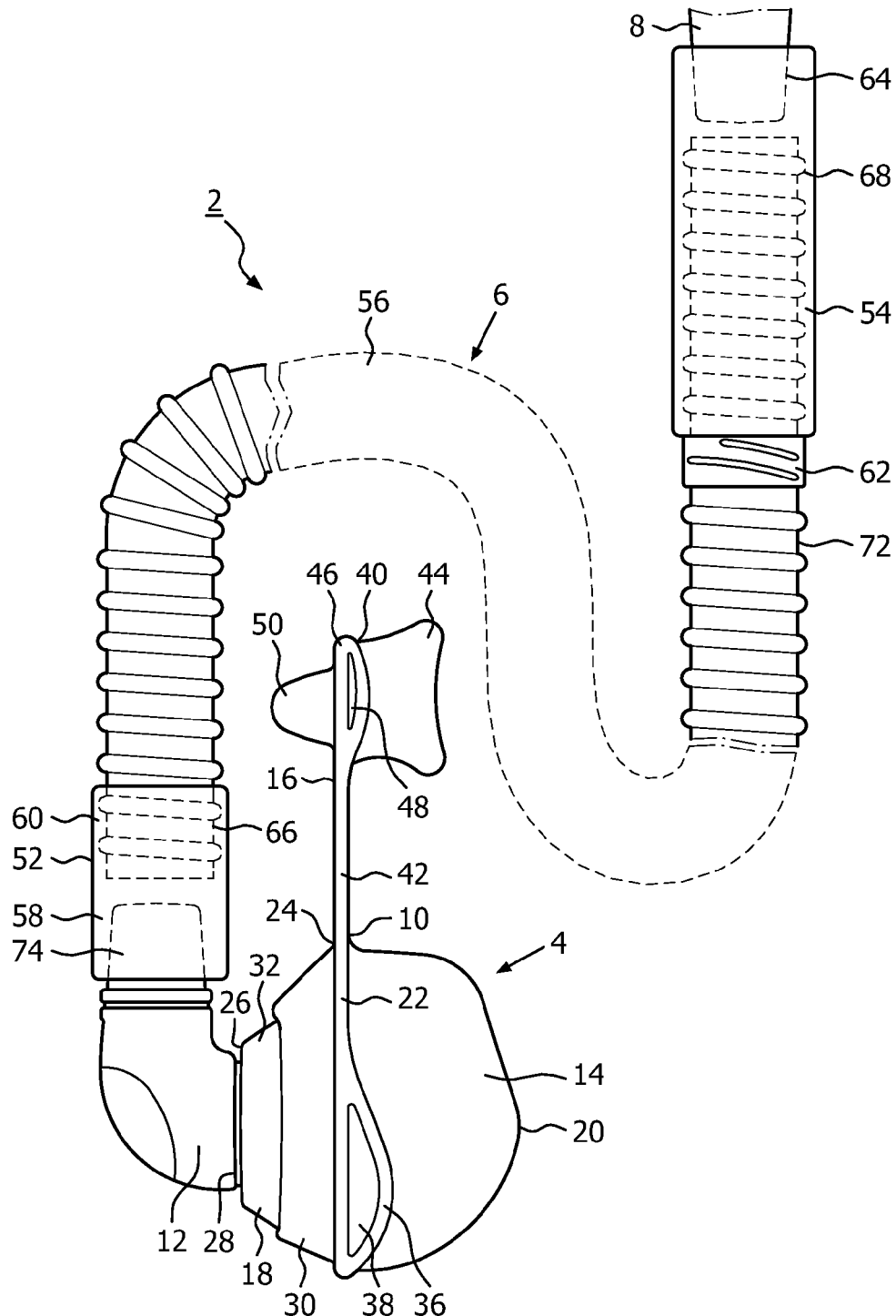
FIG. 1 is a side elevational view of a portable patient interface system according to one exemplary embodiment of the present invention in an expanded, operating position.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
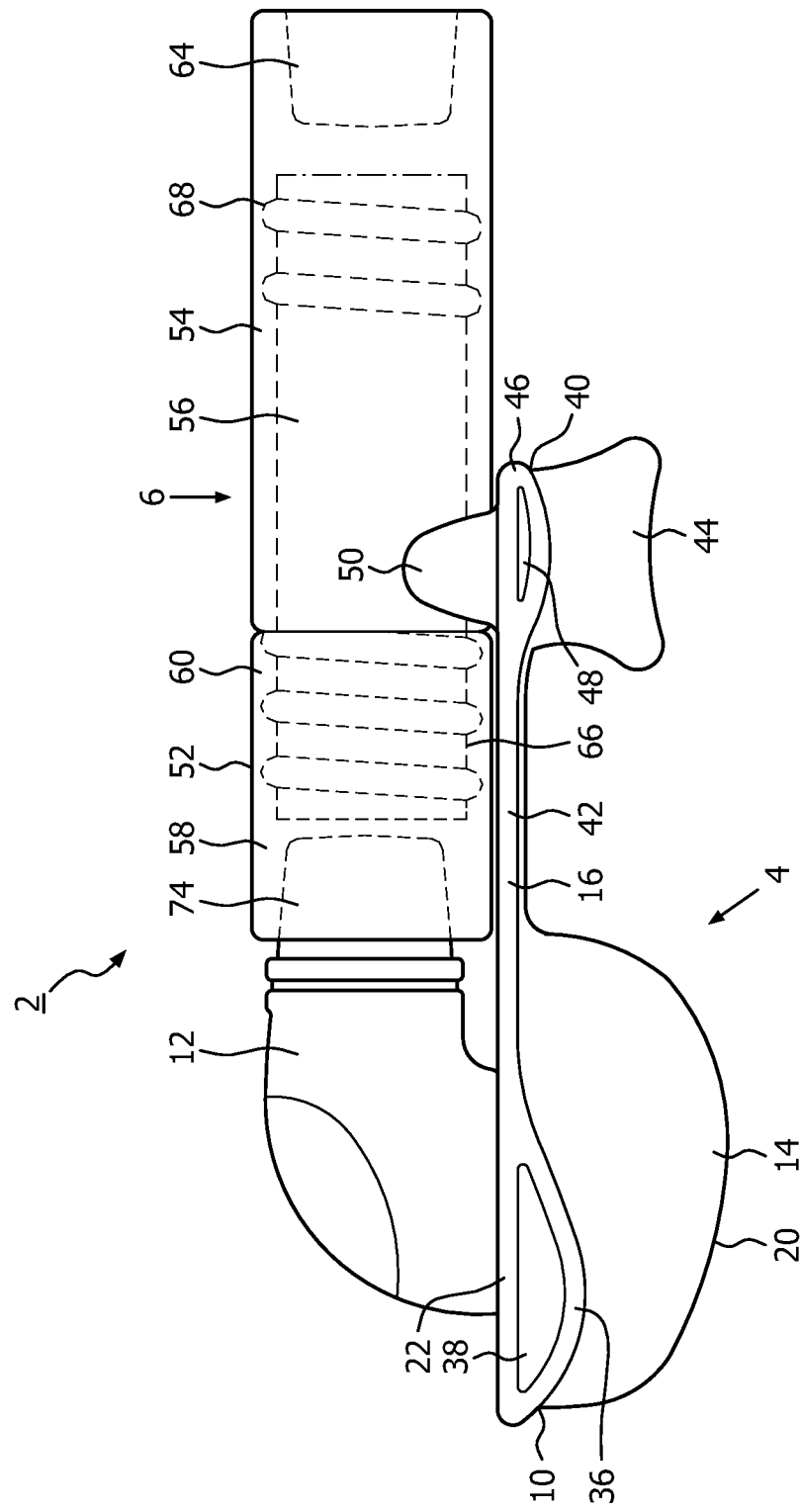
FIG. 2 is a side elevational view.
Figure 3:
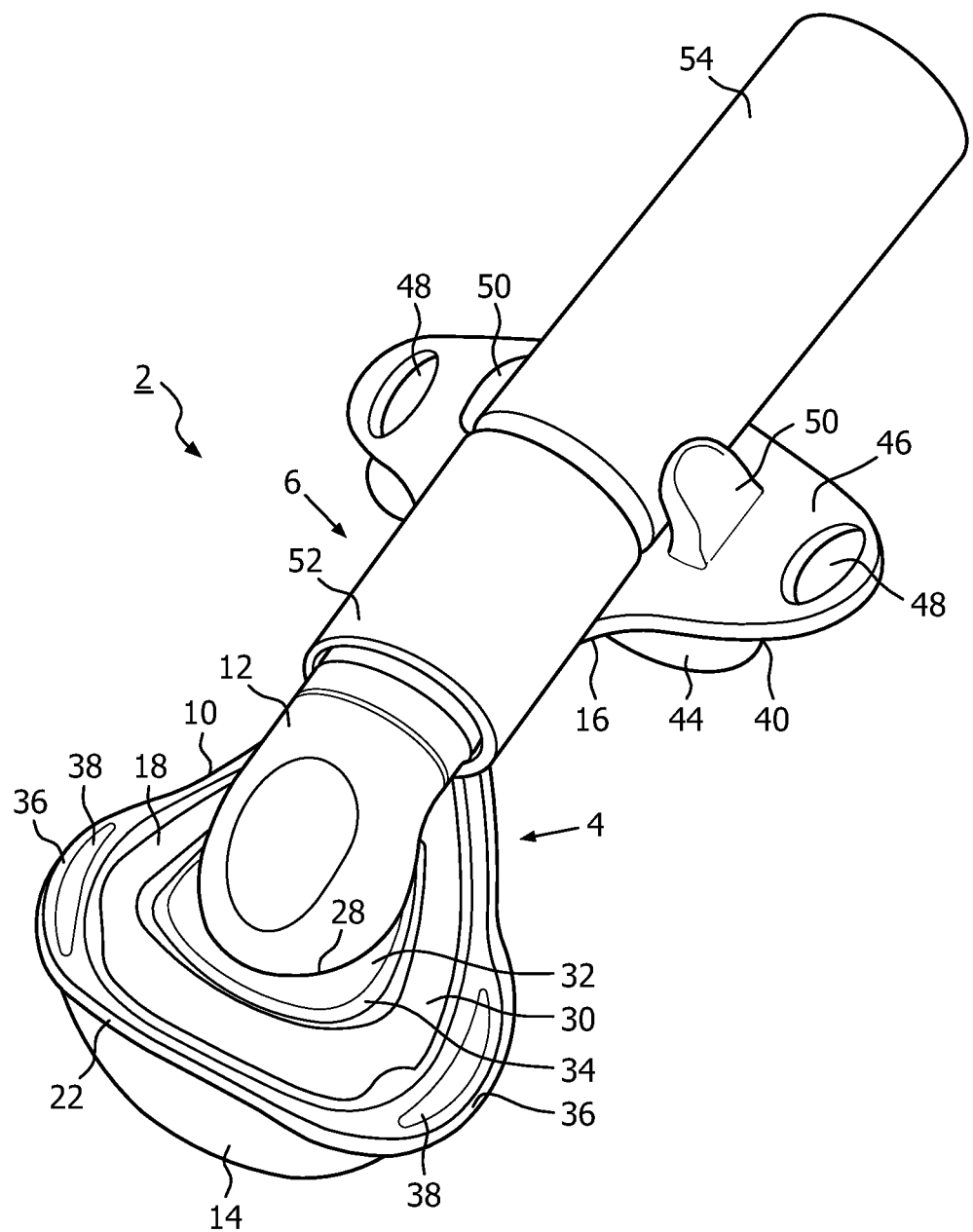
FIG. 3 is a front isometric view of the portable patient interface system of FIG. 1 in a collapsed, storage position.

FIG. 1 is a side elevational view of a portable patient interface system 2 according to one exemplary embodiment of the present invention. In FIG. 1, portable patient interface system 2 is in an expanded, operating position wherein it can be used by a patient to provide, for example, pressure support therapy. FIG. 2 is a side elevational view and FIG. 3 is a front isometric view of portable patient interface system 2 in a collapsed position. As seen in FIGS. 2 and 3, in the collapsed position, the size and profile of the portable patient interface system 2 has been greatly reduced and each of the component thereof has been secured against unwanted movement, which makes for easier and more convenient storage, packing and/or transport of patient interface system 2.

Portable patient interface system 2 includes a collapsible patient interface device 4 that is operatively coupled to collapsible hose assembly 6. Collapsible hose assembly 6 is structured to be selectively coupled to a gas output 8 of a suitable pressure generating device that is structured to generate a flow of breathing gas for delivery to the patient. Such a pressure generating device may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Collapsible hose assembly 6 is structured to communicate the flow of breathing gas output from gas outlet 8 to patient interface device 4.

Patient interface device 4 includes a mask 10 that is fluidly coupled to an elbow conduit 12. Elbow conduit 12 is structured to be coupled to collapsible hose assembly 6 which, as described above, is able to be selectively coupled to a pressure generating device. In the illustrated embodiment, mask 10 is a nasal mask. However, other types of masks, such as a nasal/oral mask or a full face mask, which facilitate the delivery of a flow of breathing gas to the airway of a patient may be used as mask 10 while remaining within the scope of the present invention.

Mask 10 includes a sealing cushion 14, a frame 16 and a collapsible faceplate 18. Frame 16 is made of a rigid or semi-rigid material, such as, without limitation, plastic, and, in the exemplary embodiment, is generally flat and has a slim profile. In one non-limiting particular embodiment, frame 16 is made of a rigid plastic and has a cross-sectional thickness of about 1.2 to 2.5 mm.

Both sealing cushion 14 and collapsible faceplate 18 are made of a soft, flexible, elastomeric material, such as, without limitation, silicone rubber, an appropriately soft thermoplastic elastomer, or any combination of such materials. The side of sealing cushion 14 opposite a sealing surface 20 of sealing cushion 14 is coupled to a rear side of an annular portion 22 of frame 16. As used herein, the term "annular" shall mean having the form of a circular or non-circular ring defining an enclosed area. As seen in FIG. 3, in the illustrated embodiment, annular portion 22 of frame 16 has a generally triangular shape. A first end 24 of collapsible faceplate 18 is coupled to a front side of annular portion 22 of frame 16. In the exemplary embodiment, sealing cushion 14 and collapsible faceplate 18 are over-molded onto frame 16 from the same material. In addition, a second end 26 of collapsible faceplate 18 is coupled to a first end 28 of elbow conduit 12. Sealing cushion 14, collapsible faceplate 18 and elbow conduit 12 are in fluid communication with one another.

As shown in FIG. 2, collapsible faceplate 18 is structured to be able to be collapsed and received within a chamber defined by the interior of sealing cushion 14 and annular portion 22 of frame 16 in response to a force being applied to collapsible faceplate 18 generally in the direction of the arrow shown in FIG. 2 (in the exemplary embodiment, at least a portion of collapsible faceplate 18 will pass through annular portion 22 and into interior of sealing cushion 14 when collapsed). In addition, in the exemplary embodiment, in this collapsed position, at least a portion of first end 28 of elbow conduit 12 will be received within the chamber defined by the interior of sealing cushion 14 and annular portion 22.

In the illustrated embodiment, collapsible faceplate 18 has a two-tiered structure including a first tier 30 that is coupled to the front side of annular portion 22 and a second tier 32 that is coupled to first end 28 of elbow conduit 12. First tier 30 and second tier 32 are coupled to one another in a manner wherein second tier 32 is structured to collapse within the outer boundary of first tier 30 when collapsible faceplate 18 is caused to collapse. In the exemplary embodiment, first tier 30 and second tier 32 are coupled to one another by a transition portion 34 (FIG. 3) that includes a pleat (fold) or local thin section to encourage second tier 32 to roll inside first tier 30 (second tier 32 will roll inside out and rest on first tier 30). In addition, collapsible faceplate 18 may include more than two tiers. If there are more than two tiers, beginning with the inner-most tier, each will collapse and roll inside and/or on top of the adjacent tier.

In addition, frame 16 includes a pair of connecting members 36 extending from opposites side of annular portion 22, wherein each connecting member 36 includes a loop 38 which is structured to receive a respective lower headgear strap of a headgear assembly (not shown) for securing patient interface device 4 to the head of the patient. Frame 16 further includes forehead support 40 attached to extension member 42 extending from annular portion 22. Forehead support 40 includes forehead cushion 44 that is coupled to support frame 46. Forehead cushion 44 is made of a soft, flexible, elastomeric material, such as, without limitation, silicone rubber, an appropriately soft thermoplastic elastomer, or any combination of such materials, and, in the exemplary embodiment, is over-molded onto support frame 46. Forehead support 40 is structured to provide additional support for patient interface device 4 by engaging the forehead of the patient. Support frame 46 includes loops 48 provided at opposite ends thereof. Each loop 48 is structured to receive a respective upper headgear strap of a headgear assembly (not shown) for securing patient interface device 4 to the head of the patient. In addition, a pair of tabs 50 extend from a front side of support frame 46, and are structured to hold collapsible hose assembly 6 (described in greater detail) herein when patient interface device 4 is in the collapsed, storage position.

Figure 4:
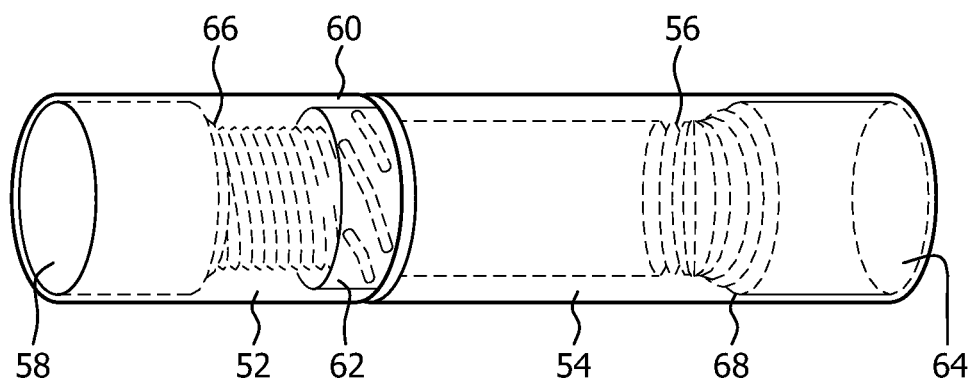
FIG. 4 is a top plan view of a collapsible hose assembly forming part of the portable patient interface system of FIG. 1.

As seen in FIGS. 1 and 4 (which is a top plan view of collapsible hose assembly 6), collapsible hose assembly 6 includes a first tube portion 52, a second tube portion 54 and a collapsible hose 56. First tube portion 52 includes a female fitting 58 at a first end thereof, and an internal threaded portion 60 at a second end thereof opposite the first end (the remainder of first tube portion 52 being hollow). As seen in FIGS. 1-3, female fitting 58 receives and sealingly engages second end 74 of elbow conduit 12. Second tube portion 54 includes threaded portion 62 extending from a first end thereof, and female fitting 64 at a second end thereof opposite the first end (the remainder of second tube portion 54 being hollow). In the exemplary embodiment, female fittings 58 and 64 are each a 22 mm female fitting, although other sizes may also be used.

Figure 5:
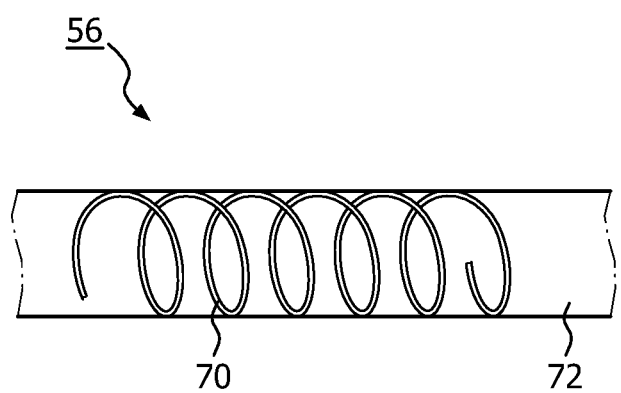
FIG. 5 is a top plan view of an exemplary embodiment of a portion of a collapsible hose forming part of the collapsible hose assembly of FIG. 4.

Collapsible hose 56 includes first end 66 that is coupled to female fitting 58 and second end 68 that is coupled to female fitting 64. Collapsible hose 56 is structured to be able to be longitudinally collapsed so that it can go from a maximum length, e.g., six feet, to some small fraction of the maximum length, e.g., four to six inches. Referring to FIG. 5, which is a top plan view of a portion of collapsible hose 56 according to one exemplary, non-limiting embodiment, collapsible hose 56 includes a longitudinally collapsible helix portion 70 surrounded by a flexible outer skin portion 72. In the exemplary embodiment, helix portion 70 is made of a highly pliable material, such as, without limitation, a metal wire coated with a thin layer of elastic material (mainly for protection), such as, without limitation, metallocene, polypropylene, EVA, Hytrel™ or some other TPE. Also in the exemplary embodiment, outer skin portion 72 is made of an elastic material such as, without limitation, metallocene, polypropylene, EVA, Hytrel™ or some other TPE, and is air-tight, FIG. 1 shows collapsible hose assembly 6 in its expanded state for when patient interface system 2 is to be used by the patient. More specifically, in the expanded state, first tube portion 52 and second tube portion 54 are separated from one another and collapsible hose 56 is allowed to expand to up to it maximum length. In this state, female fitting 64 is able to receive and sealingly engage gas outlet 8 of a pressure generating device so that breathing gas can be delivered to the airway of the patient through collapsible hose assembly 6 and patient interface device 4. FIGS. 2, 3 and 4 show collapsible hose assembly 6 in its collapsed state for when patient interface system 2 is to be stored, packed and/or transported. In the collapsed state, collapsible hose 56 is collapsed within the hollow interior of first tube portion 52 and second tube portion 54, and first tube portion 52 and second tube portion 54 are coupled to one another through threaded engagement between internal threaded portion 60 and threaded portion 62. Second tube portion 54 may then be inserted and held between tabs 50 until the next time collapsible hose assembly 6 is need to be expanded. Other interlock mechanisms may be used instead of the threaded engagement just described. For example, the interlock may be a friction fit between first tube portion 52 and second tube portion 54, a mechanical lock between the two tube portions, or any push-and-turn locking mechanism. In addition other attaching/locking mechanisms can be provided for tabs 50. In addition, this locking mechanism or tabs 50 can be configured so as to secure the first and/or second tube portion to the mask frame and/or forehead support.

Thus, portable patient interface system 2 provides an interface system that may be used with non-invasive ventilation and pressure support systems that can be selectively placed in either a collapsed position having a small size and profile that facilitates storage, packing and/or transport of the interface system or an expanded, operating position wherein the interface system can be used to effectively provide therapy.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface system, comprising:
    a frame;
    a cushion coupled to a first side of the frame;
    a collapsible faceplate coupled to a second side of the frame opposite the first side; and
    a longitudinally collapsible hose structured to be in fluid communication with the collapsible faceplate and the cushion, wherein the frame includes an attaching mechanism structured to secure the longitudinally collapsible hose to the frame when a first end of the longitudinally collapsible hose is in fluid communication with the collapsible faceplate and the collapsible faceplate is in a collapsed condition in which at least a portion of the collapsible faceplate is received within a chamber defined by an interior of the cushion, wherein the longitudinally collapsible hose is provided in a collapsible hose assembly having a first tube portion and a second tube portion, wherein the first tube portion and the second tube portion are selectively connectable to one another, wherein the longitudinally collapsible hose, when collapsed, is structured to be held within the first tube portion and the second tube portion, and wherein the attaching mechanism is structured to secure the collapsible hose assembly to the frame.

2. The patient interface system according to claim 1, wherein the first tube portion has a first connector at a first end thereof and the second tube portion has a second connector at a first end thereof, wherein the first end of the collapsible hose is coupled to the first connector and a second end of the collapsible hose is coupled to the second connector.

3. The patient interface system according to claim 2, further comprising a coupling connector fluidly coupled to the collapsible faceplate, wherein the first connector is coupled to the coupling connector and the second connector is structured to be selectively coupled to a gas outlet of a pressure generating device.

4. The patient interface system according to claim 2, wherein the first tube portion has a first threaded portion at a second end thereof and the second tube portion has a second threaded portion at a second end thereof, and wherein the first tube portion and the second tube portion are selectively connectable to one another through engagement between the first threaded portion and the second threaded portion.

5. The patient interface system according to claim 1, wherein the longitudinally collapsible hose includes a longitudinally collapsible helix portion surrounded by a flexible outer skin portion.

6. The patient interface system according to claim 1, wherein the cushion and collapsible faceplate are coupled to an annular portion of the frame, wherein the frame includes an extension member extending from the annular portion and a forehead support coupled to the extension member, and wherein the attaching mechanism comprises a plurality of tabs provided on the forehead support and structured to receive and hold the collapsible hose assembly.

7. The patient interface system according to claim 6, wherein the plurality of tabs are structured to receive and hold the second tube portion.

8. The patient interface system according to claim 1, wherein the cushion and collapsible faceplate are coupled to an annular portion of the frame, wherein the collapsible faceplate is structured to be collapsed and received within a chamber defined by an interior of the cushion and the annular portion responsive to a force being applied to the collapsible faceplate.

9. The patient interface system according to claim 8, wherein the frame is made of a rigid or semi-rigid material and the cushion and the collapsible faceplate are made of an elastomeric material.

10. The patient interface system according to claim 9, wherein the collapsible faceplate includes a first tier coupled to the annular portion and a second tier coupled to the first tier, wherein the second tier is structured to collapse within and outer boundary of the first tier when the collapsible faceplate is caused to collapse.

* * * * *